United States Patent
Ishii et al.

(10) Patent No.: US 9,750,476 B2
(45) Date of Patent: Sep. 5, 2017

(54) WIRELESS FOOT SWITCH AND X-RAY DIAGNOSIS SYSTEM

(71) Applicant: TOSHIBA MEDICAL SYSTEMS CORPORATION, Otawara-shi (JP)

(72) Inventors: Takanobu Ishii, Otawara (JP); Tomoko Ishizaki, Utsunomiya (JP); Arata Komuro, Yaita (JP); Masahiko Ono, Nasushiobara (JP); Kouji Noda, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 384 days.

(21) Appl. No.: 14/627,369

(22) Filed: Feb. 20, 2015

(65) Prior Publication Data
US 2015/0250439 A1 Sep. 10, 2015

(30) Foreign Application Priority Data
Mar. 4, 2014 (JP) ................................ 2014-041816

(51) Int. Cl.
H05G 1/54 (2006.01)
A61B 6/00 (2006.01)

(52) U.S. Cl.
CPC . *A61B 6/54* (2013.01); *A61B 6/56* (2013.01)

(58) Field of Classification Search
CPC .............. A61B 6/542; A61B 6/54; A61B 6/56
USPC ......................................... 378/114–117, 205
See application file for complete search history.

(56) References Cited

U.S. PATENT DOCUMENTS

2005/0207534 A1 9/2005 Petrick et al.
2010/0124366 A1* 5/2010 Shields ................ A61B 5/7475
382/131

FOREIGN PATENT DOCUMENTS

JP 2005-270656 10/2005

* cited by examiner

*Primary Examiner* — Courtney Thomas
(74) *Attorney, Agent, or Firm* — Oblon, McClelland, Maier & Neustadt, L.L.P.

(57) ABSTRACT

A wireless foot switch according to one embodiment includes a battery unit, a switch unit, a controller, and a state switcher. The battery unit supplies power. The switch unit provides input to an X-ray diagnosis apparatus. The controller transmits by radio, to X-ray diagnosis apparatus, information input by the switch unit. Based on an external signal from the outside of the X-ray diagnosis apparatus, the state switcher causes the controller to transition from a resting state to an operational state.

14 Claims, 16 Drawing Sheets

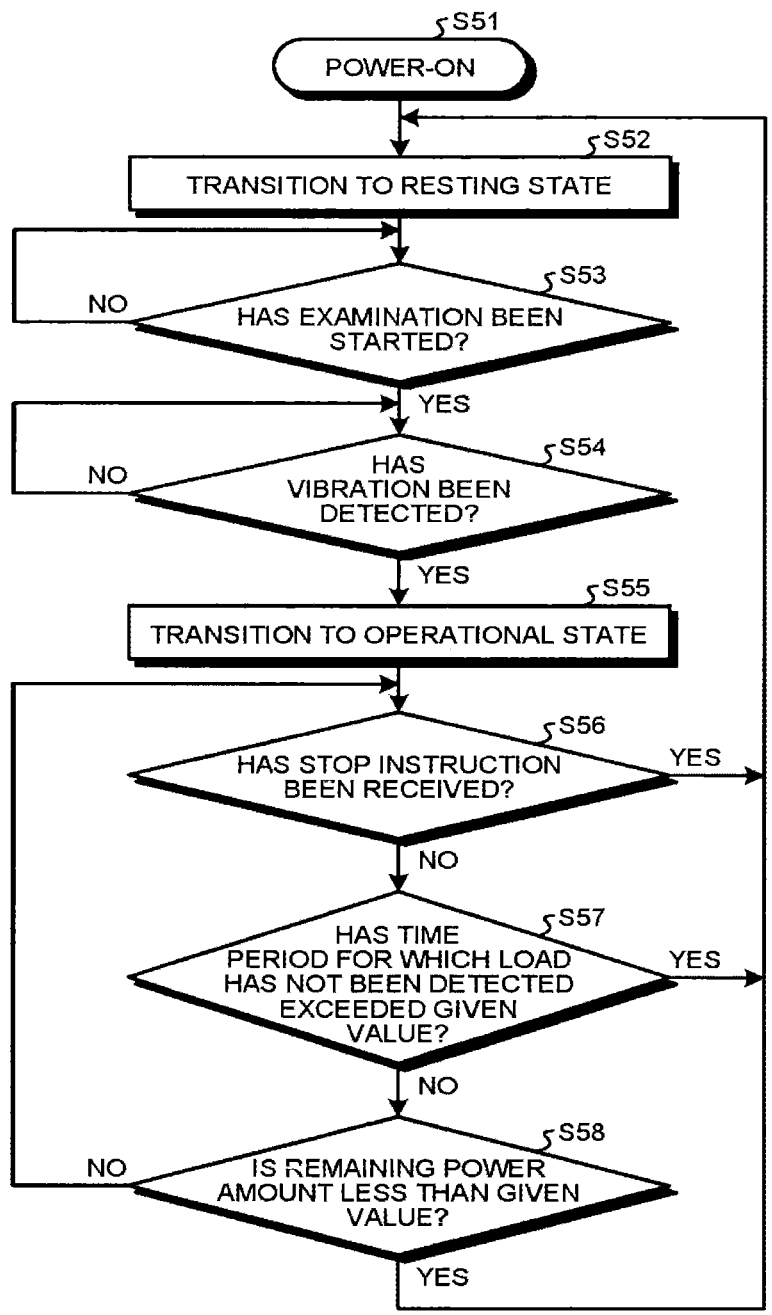

WIRELESS FOOT SWITCH AND X-RAY DIAGNOSIS SYSTEM

CROSS-REFERENCE TO RELATED APPLICATION(S)

This application is based upon and claims the benefit of priority from Japanese Patent Application No. 2014-041816, filed on Mar. 4, 2014; the entire contents of which are incorporated herein by reference.

FIELD

Embodiments described herein relate generally to a wireless foot switch and an X-ray diagnosis system.

BACKGROUND

X-ray diagnosis apparatuses are present, which use X-rays for diagnosis of a subject. In some cases, an X-ray diagnosis apparatus is used in an examination room during a medical procedure, and a procedure performer sometimes operates the X-ray diagnosis apparatus with a foot switch. As a foot switch for such an X-ray diagnosis apparatus, a wireless foot switch has been proposed, which transmits signals to the X-ray diagnosis apparatus by radio. A wireless foot switch is advantageous in that the installation position thereof can be easily changed according to the move of the procedure performer.

Because of the need to use a built-in battery for putting the wireless foot switch into operation, however, a wireless foot switch is inconvenient for its limited operating time. Although using a larger built-in battery may be effective in extending the operating time, a larger built-in battery increases the weight of a wireless foot switch and makes the wireless foot switch difficult to move.

BRIEF DESCRIPTION OF THE DRAWINGS

FIG. 19 is a flowchart diagram exemplifying operations of the wireless foot switch according to the sixth embodiment.

DETAILED DESCRIPTION

According to embodiment, a wireless foot switch comprising, a battery unit, a switch unit, a controller and a state switcher. The battery unit that supplies power. The switch unit that provides input to an X-ray diagnosis apparatus. The controller that transmits information to the X-ray diagnosis apparatus by radio, the information having been input by the switch unit. The state switcher that, based on an external signal from the outside of the X-ray diagnosis apparatus, causes the controller to transition from a resting state to an operational state.

The following describes embodiments of a wireless foot switch and an X-ray diagnosis system according to the present application with reference to the drawings. Here, the wireless foot switch and the X-ray diagnosis system according to the present application are configured to enable the wireless foot switch to transition from a resting state to an operational state at appropriate timings, thereby eliminating inconvenience when a procedure performer operates it, and also enable the wireless foot switch to operate with reduced power consumption. Specifically, the wireless foot switch and the X-ray diagnosis system according to the present application cause the wireless foot switch to transition from the resting state to the operational state, on the basis of an external signal received by an X-ray diagnosis apparatus from the outside or on the basis of an external stimulus provided to the wireless foot switch. These operations are described below in order.

Figure 1:
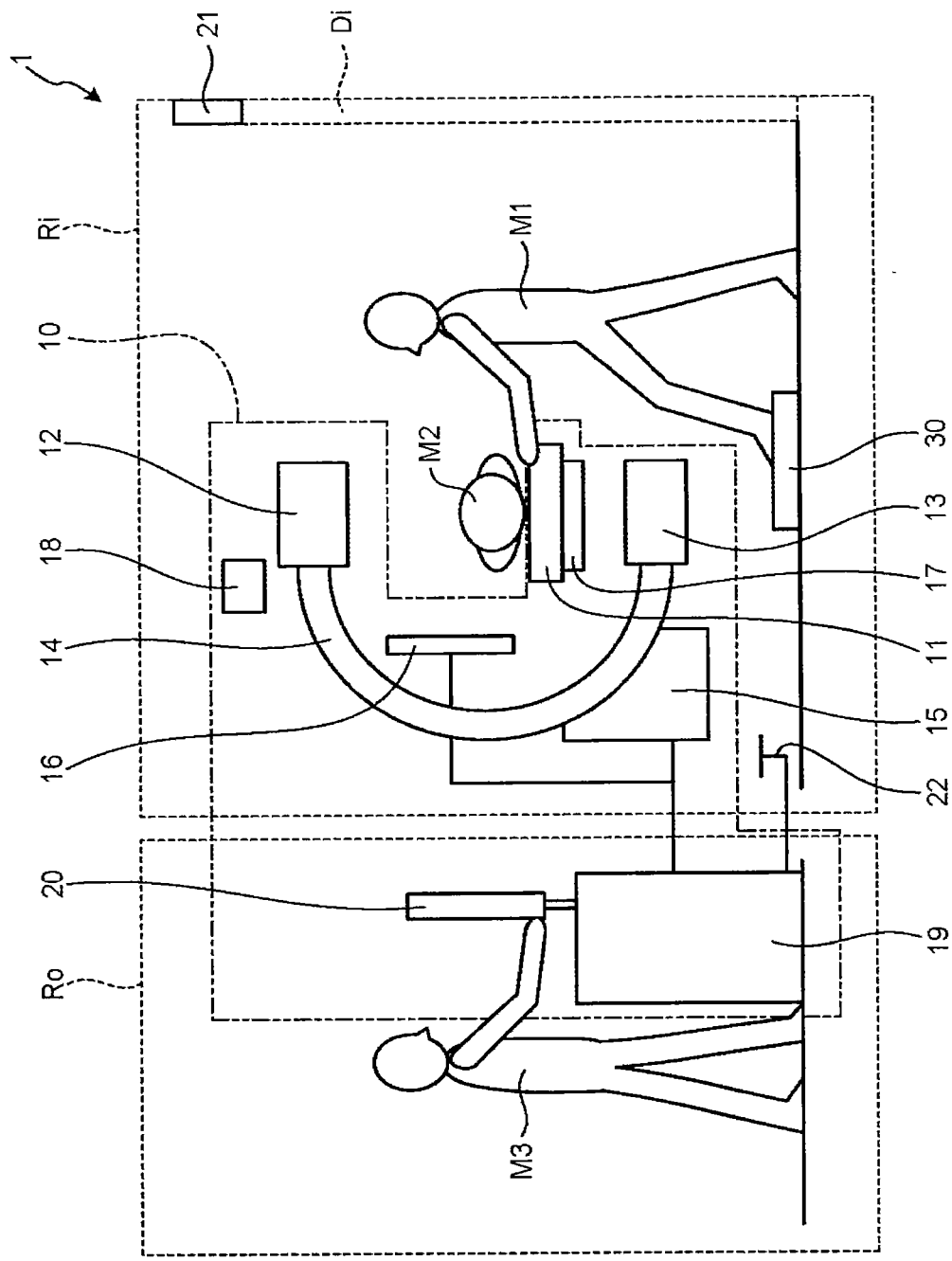
FIG. 1 is a diagram exemplifying an X-ray diagnosis system according to a first embodiment.
Figure 2:
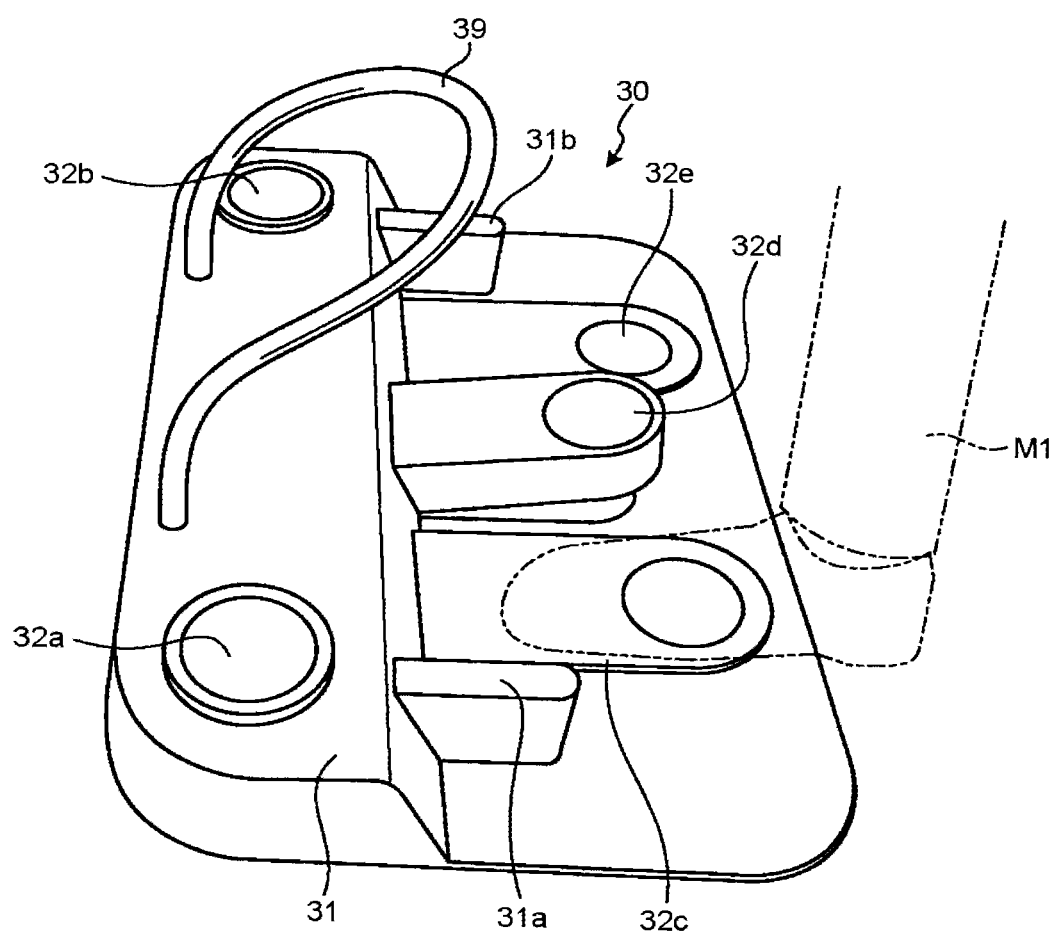
FIG. 2 is a perspective view exemplifying a wireless foot switch according to the first embodiment.
Figure 3:
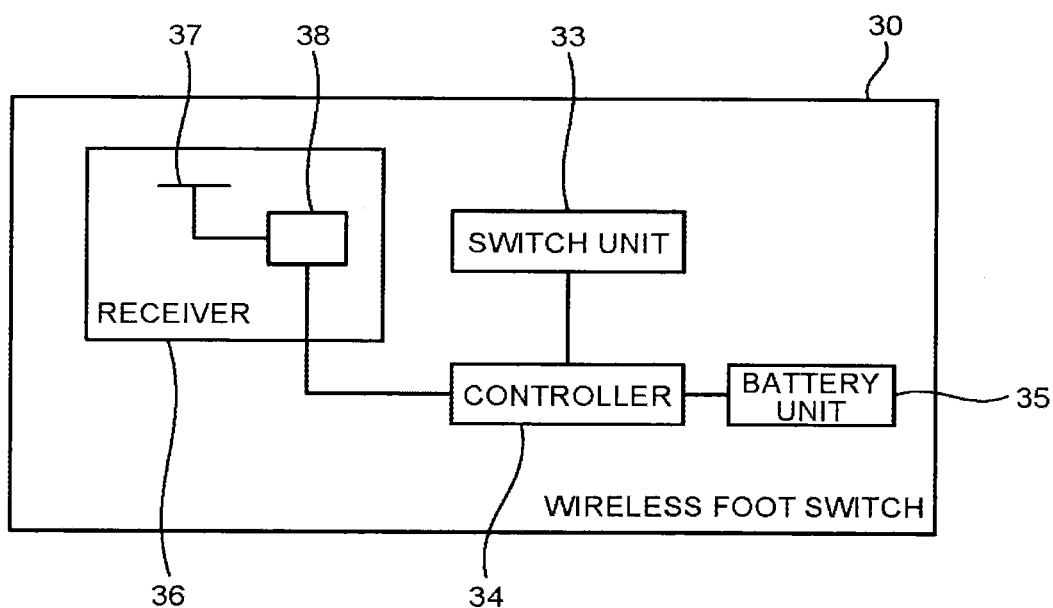
FIG. 3 is a block diagram exemplifying the wireless foot switch according to the first embodiment.

First of all, a first embodiment is described. In the first embodiment, a case where the state is caused to transition on the basis of a signal indicating that a door of an examination room is closed, which is the external signal, is described. FIG. 1 is a diagram exemplifying an X-ray diagnosis system according to this embodiment. FIG. 2 is a perspective view exemplifying a wireless foot switch according to this embodiment. FIG. 3 is a block diagram exemplifying the wireless foot switch according to this embodiment.

The X-ray diagnosis system according to this embodiment is described first. As illustrated in FIG. 1, an X-ray diagnosis system 1 according to this embodiment is provided in such a manner that, while one part thereof is in an examination room Ri, the other part thereof is in an operation room Ro. The examination room Ri is a room in which a procedure performer M1 conducts an examination and a procedure on a subject M2. The operation room Ro is a room in which an operator M3 operates the X-ray diagnosis system 1. The procedure performer M1 is, for example, a doctor or an X-ray examination technologist.

The X-ray diagnosis system 1 includes an X-ray diagnosis apparatus 10. The X-ray diagnosis apparatus 10 is, for example, an X-ray imaging apparatus. The X-ray diagnosis apparatus 10 includes: a bed 11 that supports the subject M2; an X-ray tube 12 that radiates X-rays to the subject M2 lying on the bed 11; a detector 13 that detects X-rays having transmitted through the subject M2; an C-shaped arm 14 that supports the X-ray tube 12 and the detector 13 at a position interposing the subject M2 in between; a support mechanism 15 that rotatably support the C-shaped arm 14; an examination room panel 16 from which to control the X-ray diagnosis system 1 from the inside of the examination room Ri and on which information such as an image is displayed; a bed driving mechanism 17 that moves the bed 11; an X-ray control mechanism 18 that controls the intensity and the like of X-rays output from the X-ray tube 12; a control unit 19 that controls the entirety of the X-ray diagnosis system 1 and generates and stores an X-ray image on the basis of detection results from the detector 13; and an operation room panel 20 from which to control the X-ray diagnosis system 1 from the inside of the operation room Ro and on which to display information such as an image.

Some of the components of the X-ray diagnosis apparatus 10, such as the bed 11, the X-ray tube 12, the detector 13, the C-shaped arm 14, the support mechanism 15, the examination room panel 16, the bed driving mechanism 17, and the X-ray control mechanism 18, are arranged in the examination room Ri. On the other hand, the control unit 19 and the operation room panel 20 are arranged in the operation room Ro. The respective components of the X-ray diagnosis apparatus 10 are connected to one another so as to be able to operate in synchronization with one another. Note that the X-ray diagnosis apparatus 10 may include a component other than the above ones.

The examination room Ri is a room inside which X-rays are radiated by the X-ray diagnosis apparatus 10. For this reason, the X-ray diagnosis system 1 includes a door sensor 21 that detects a state in which a door Di of the examination room Ri is closed. A detection result from the door sensor 21 is input to, for example, the control unit 19. This configuration enables the control unit 19 to confirm whether the door Di of the examination room Ri has been opened or closed.

The X-ray diagnosis system 1 according to this embodiment further includes an antenna 22 that is connected to the control unit 19 and arranged in the examination room Ri. The control unit 19 issues an "examination start signal" and a "door switch signal" by radio through the antenna 22. The "examination start signal" indicates that an examination has started. The "door switch signal" indicates that the door Di is closed. The X-ray diagnosis system 1 still further includes a wireless foot switch (hereinafter, also simply referred to as "foot switch") 30, which is used by the procedure performer M1 to operate the X-ray diagnosis apparatus 10 with a foot thereof.

Next, the wireless foot switch according to this embodiment is described. As illustrated in FIG. 2 and FIG. 3, the wireless foot switch 30 has a substantially plate-like shape in which the hinder part has a higher height than the fore part. The foot switch 30 includes, for example, a robust housing 31 made of metal.

On the top surface of the housing 31, at least one panel, for example, five pedals 32a to 32e (hereinafter, each representatively referred to as "pedal 32") is provided. For example, on the top surface of the housing 31, the pedals 32a and 32b are arranged in a pair at the two left and right ends of the higher region located at the hinder part from the procedure performer M1. The pedals 32c and 32e are arranged in a pair in the lower region located at the fore part. Additionally, the pedal 32d is arranged between the pedal 32c and the pedal 32e. Functions can be assigned to the respective pedals 32 in any desirable manner. Furthermore, guide portions 31a and 31b having higher heights than their surrounding portions are formed, on the top surface of the housing 31, in regions that abut opposing sides of a region corresponding to the pedals 32c, 32d, and 32e.

Each of the pedals 32 is configured to be movable upward and downward or rotatable within a certain range. The pedal 32 is usually positioned at the upper limit of a range it can move, and moves to the lower limit by being pushed by the procedure performer M1 with a foot thereof. To each of the pedals 32, a contact mechanism (not illustrated) is attached, which converts the position of the pedal 32 into and an electric signal. All of the pedals 32 and the contact mechanism constitute a switch unit 33.

The housing 31 includes a controller 34 built therein and connected to the switch unit 33. The controller 34 receives input of an electric signal from the switch unit 33, generates a predetermined instruction signal based on the electric signal, and transmits this instruction signal to the X-ray diagnosis apparatus 10 by radio. The controller 34 conducts communication through radio waves that is based on, for example, Bluetooth (registered trademark) with the X-ray diagnosis apparatus 10. The housing 31 further includes a battery unit 35 built therein and configured to supply power to the controller 34. The battery unit. 35 includes a rechargeable battery.

The state of the controller 34 can be either operational or resting. When being active, the controller 34 maintains radio communication with the X-ray diagnosis apparatus 10, and can transmit an instruction signal by radio immediately after an operation is performed on the pedal 32. However, when being active, the controller 34 needs to maintain the radio communication and keep the switch unit 33 active at the same time, thereby consuming power even when the pedals 32 are not being operated. On the other hand, when being in the resting state, the controller 34 does not conduct radio communication with the X-ray diagnosis apparatus 10. Therefore, the standby power can be suppressed. However, transmission of an instruction signal needs the controller 34 to transition from the resting state to the operational state, and the transition needs a certain amount of time.

The foot switch 30 includes a receiver 36 as a trigger unit (also referred to as a state switcher) that causes the controller 34 to transition from the resting state to the operational state on the basis of a change of external environment of the foot switch 30. The receiver 36 includes an antenna 37 and a reception circuit 38. The reception circuit 38 is connected to the antenna 37 and the controller 34. This connection enables the reception circuit 38 to generate a trigger signal and output the generated trigger signal to the controller 34 upon receiving, through the antenna 37, a radio signal transmitted from the antenna 22. The receiver 36 does not receive power supply from the battery unit 35 and operates by converting part of the received radio signal into power. For example, the receiver 36 includes an antenna built therein. This antenna is for use in a crystal radio. Thus, the receiver 36 can be put into operation without power from the battery unit 35.

Furthermore, a protector 39 is provided on the top surface of the hinder part of the housing 31. The protector 39 is formed, for example, in such a manner that both ends of a metal pipe curved into a U shape are joined to the housing 31. A longitudinally central portion of the pipe forms the upper part of the protector 39 as a loop-like part, and is bent frontward. The protector 39 is a bar for preventing the pedals 32 from being pushed with the self weight of the foot switch 30 acting thereon when the foot switch 30 is dropped or turned over. Furthermore, although a power code may be connected to the foot switch 30 when the battery unit 35 is charged, any codes and similar items are not connected thereto at least when the foot switch 30 is being used as a switch.

Figure 4:
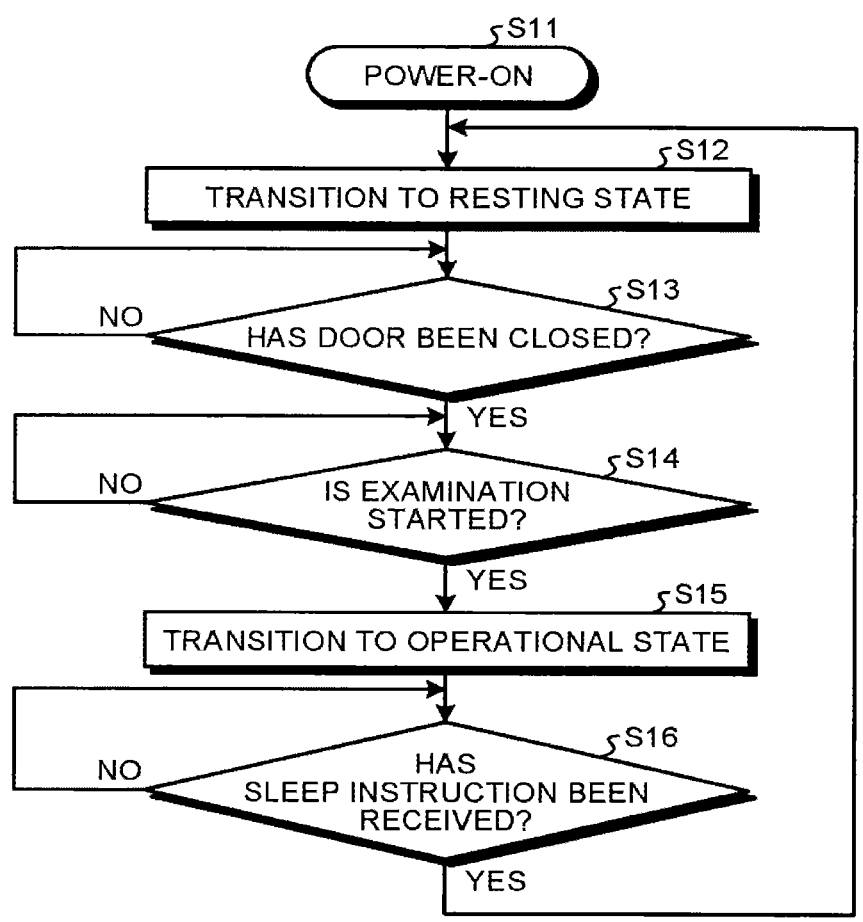
FIG. 4 is a flowchart diagram illustrating operations of the wireless foot switch according to the first embodiment.

Next, operations of the thus configured wireless foot switch and X-ray diagnosis system according to this embodiment are described. FIG. 4 is a flowchart diagram illustrating operations of the wireless foot switch according to this embodiment.

Operations of the wireless foot switch according to this embodiment are described first. As illustrated in Step S11 in FIG. 4, the foot switch 30 starts up when the power is turned on to the foot switch 30. Here, the power-on of the foot switch 30 at Step S11 may be executed in response to operation of a switch by the procedure performer M1 or the operator M3, or may be configured so that the foot switch 30 can be automatically powered on the basis of the charging level thereof. In the latter case, for example, a lower limit value is previously set for the charging level of the foot switch 30, and the foot switch 30 enters into a power-on state when the charging level of the foot switch 30 exceeds the lower limit value. In other words, as long as the charging level exceeds the lower limit value, the foot switch 30 automatically keeps being powered on, and the procedure performer M1 or the operator M3 does not need to go to the trouble of performing a power-on operation. Note that the foot switch 30 is powered off when the charging level is lower than the lower limit value.

Subsequently, the controller 34 transitions to the resting state, as illustrated in Step S12. Upon occurrence of this transition, the controller 34 cuts off radio communication with the X-ray diagnosis apparatus 10, and output of instruction signals is disabled even if operations are performed on the pedals 32. At the same time, the standby power decreases, so that reduction of power stored in the battery unit 35 can be prevented.

The process then proceeds to Step S13, where the controller 34 confirms whether the door Di of the examination room Ri has been closed. Specifically, if the door Di is closed, the door sensor 21 detects that state, and outputs the detection result to the control unit 19 of the X-ray diagnosis apparatus 10. The control unit 19 issues, through the antenna 22, a "door switch signal" indicating that the door Di is closed. The reception circuit 38 of the foot switch 30 receives this door switch signal through the antenna 37, and outputs the door switch signal to the controller 34. As a result, the controller 34 confirms that the door Di has been closed. At this step, the receiver 36 operates by converting part of the door switch signal into power.

If the door Di has been closed, the process proceeds to Step S14, where the foot switch 30 confirms whether the X-ray diagnosis system 1 is in a state ready for "starting an examination". Specifically, when a command for "starting an examination" is input to the X-ray diagnosis apparatus 10, an "examination start signal" is issued through the antenna 22. The reception circuit 38 of the foot switch 30 receives this "examination start signal" through the antenna 37, and outputs it to the controller 34. As a result, the controller 34 confirms that the X-ray diagnosis system 1 is in a state ready for "starting an examination". At this step, the receiver 36 operates by converting part of the "examination start signal" into power. The above-described door switch signal and the "examination start signal" are radio signals indicating that the X-ray diagnosis apparatus 10 has become operable to radiate X-rays.

Step S14 may be carried out before Step S13 with the order of Steps S13 and S14 reversed. Alternatively, Step S13 and Step S14 may be carried out in parallel.

If the X-ray diagnosis apparatus 10 is in a state ready for "starting an examination", the process proceeds to Step S15, where the controller 34 transitions from the resting state to the operational state. Upon occurrence of this transition, the controller 34 establishes radio communication with the X-ray diagnosis apparatus 10, and the switch unit 33 is activated. When an operation is performed on any one of the pedal 32 in this state, the controller 34 generates an instruction signal and immediately transmits this signal to the X-ray diagnosis apparatus 10 by radio. This step enables the procedure performer M1 to operate the X-ray diagnosis apparatus 10 by pushing the pedals 32 with a foot thereof.

Subsequently, the controller 34 receives a "stop instruction" from the X-ray diagnosis apparatus 10 as illustrated in Step S16, which is followed by Step S12, where the controller 34 transitions to the resting state. Thereafter, the resting state is maintained until the next input of the door switch signal and "the examination start signal".

Next, operations of the X-ray diagnosis system are described in association with action of the procedure performer or the like person.

Figure 5:
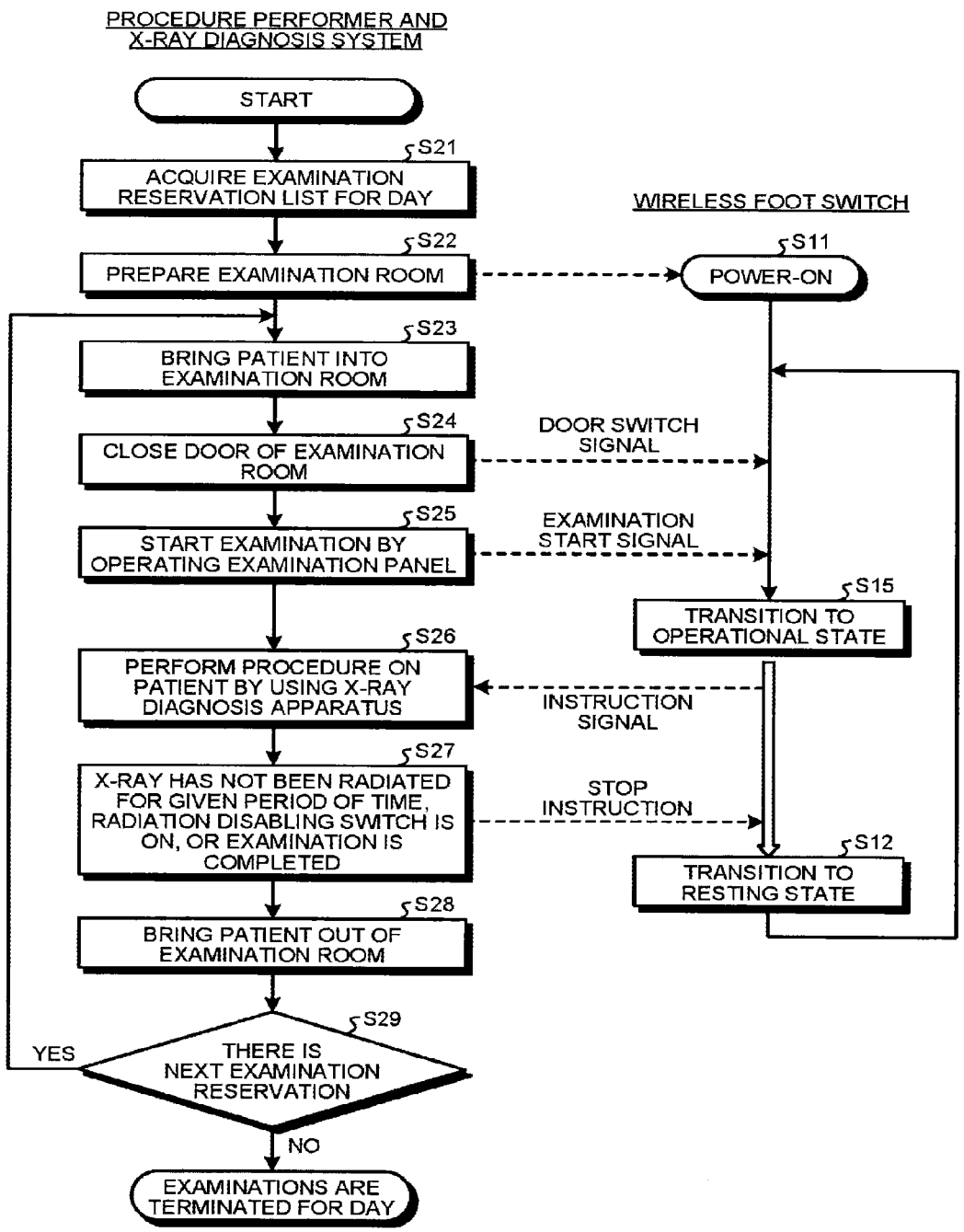
FIG. 5 is a flowchart diagram exemplifying a relation between action of a procedure performer and operations of the X-ray diagnosis system in the first embodiment.

FIG. 5 is a flowchart diagram exemplifying the relation between operations of the X-ray diagnosis system and action of the procedure performer in this embodiment. The left side of FIG. 5 outlines action of the procedure performer and operations of the X-ray diagnosis system that are performed by components thereof other than the foot switch, and the right side thereof outlines operations of the foot switch.

First, as illustrated in Step S21 in FIG. 5, the procedure performer M1 acquires an examination reservation list for the day. Subsequently, as illustrated in Step S22, the procedure performer M1 prepares the examination room Ri. The preparation includes, for example, cleaning the examination room Ri and attaching or exchanging a sterile cap. In this preparation stage, the X-ray diagnosis system 1 is started up. Subsequently, as illustrated in Step S11, the power is turned on to the foot switch 30.

Subsequently, as illustrated in Step S23, the subject M2 who is on the reservation list is brought into the examination room Ri. Thereafter, as illustrated in Step S24, the door Di of the examination room Ri is closed. At this step, the door sensor 21 detects that the door Di is closed, and outputs the detection result to the control unit 19. The control unit 19 issues a door switch signal through the antenna 22 by radio, the reception circuit 38 of the foot switch 30 receives this signal through the antenna 37.

As illustrated in Step S25, the procedure performer M1 then operates the examination room panel 16 to input an "examination start" command to the X-ray diagnosis apparatus 10. This command causes the control unit 19 to issue an "examination start signal" through the antenna 22 by radio, and the reception circuit 38 of the foot switch 30 receives this signal through the antenna 37. As a result, the controller 34 of the foot switch 30 enters into the operational state and establishes communication with the X-ray diagnosis apparatus 10, as illustrated in Step S15.

As illustrated in Step S26, the procedure performer M1 then performs a procedure on the subject M2 by using the X-ray diagnosis apparatus 10. Examples of the procedure to be performed include catheter insertion, enhancement, and X-ray fluoroscopy and photographing. When performing the procedure, the procedure performer M1 carries out work such as catheter insertion with both hands and operates the X-ray diagnosis apparatus 10 by pushing the pedals 32 of the foot switch 30 with a foot. Additionally, when a positional change of the procedure performer M1 is necessary for the procedure, the foot switch 30 is moved according to the change.

Subsequently, as illustrated in Step S27, when there has been no X-ray radiation for a given period of time, when a "radiation disabling switch" of the X-ray diagnosis apparatus 10 is turned on, or when an "end-of-examination signal" is input to the examination room panel 16 or the operation room panel 20, the control unit 19 issues a "stop instruction" through the antenna 22, and the foot switch 30 receives this stop instruction and transitions to the resting state, as illustrated in Step S12. Note that the "stop instruction" may be issued when X-ray radiation conditions have not been changed for a given period of time, instead of when there has been no X-ray radiation for a given period of time.

In some cases, a cycle from Step S25 to Step S27 is repeated more than one time. In other words, when the "examination start signal" is issued as illustrated in Step S25, the foot switch 30 transitions to the operational state as illustrated in Step S15, and, when the "stop instruction" is issued as illustrated in Step S27, the foot switch 30 transitions to the resting state as illustrated in Step S12.

Thereafter, as illustrated in Step S28, the subject M2 finished with the procedure leaves the examination room Ri. Subsequently, as illustrated in Step S29, if there is a next examination reservation in the reservation list, the process goes back to Step S23, where another subject M2 is brought into the examination room Ri, and the above-described series of work is repeated. If there is no next reservation, examinations are terminated for the day. For example, the X-ray diagnosis system 1 is stopped, the power is turned off to the foot switch 30, and charging of battery unit 35 is started by having a charging cord connected.

Next, effects of this embodiment are described. At least while being used as a foot switch, the foot switch 30 according to this embodiment is easy to carry around because it does not have any codes and similar items connected thereto. Thus, the foot switch 30 can be easily carried around when the procedure performer M1 moves, and can improve the efficiency of a procedure being performed by the procedure performer M1.

Additionally, the foot switch 30 according to this embodiment can switch between the operational state and the resting state, and therefore, can reduce power consumption thereof in such a manner as to be in the resting state while the foot switch 30 is not being used. Thus, the operating time of the foot switch 30 can be extended without upsizing of the built-in battery in the battery unit 35. Since upsizing of the built-in battery in the battery unit 35 can be avoided, the foot switch 30 does not increase in weight and the portability of the foot switch 30 is not impaired.

Furthermore, the foot switch 30 according to this embodiment includes the receiver 36, and the receiver 36 causes the controller 34 to transition from the resting state to the operational state in response to closure of the door Di of the examination room Ri and input of the "examination start" command to the X-ray diagnosis apparatus 10. This configuration enables the foot switch 30 to transition from the resting state to the operational state before the procedure performer M1 uses the foot switch 30. As a result, the procedure performer M1 can immediately start operating the X-ray diagnosis apparatus 10 with the foot switch 30 whenever desiring to operate the X-ray diagnosis apparatus 10. In other words, the procedure performer M1 can comfortably use the foot switch 30 because the procedure performer M1 does not need to perform any operation for enabling the foot switch 30 to transition from the resting state to the operational state before using the X-ray diagnosis apparatus 10 and does not perceive a time lag until the foot switch 30 becomes active. Therefore, the foot switch 30 has high operability.

In contrast, if the foot switch is not provided with the receiver 36, when the foot switch 30 is in the resting state, the procedure performer M1 needs to intentionally perform a certain operation to cause the foot switch to transition from the resting state to the operational state. Additionally, a time lag occurs between establishment of communication and transition to the operational state. For example, when the communication is performed based on the Bluetooth (registered trademark) technique, a time lag of about three seconds occurs. Such a time lag reduces the efficiency of a procedure, and adds stress to the procedure performer M1. Note that, although there are other techniques, such as ZigBee (registered trademark), that can establish communication more quickly than Bluetooth, Bluetooth is advantageous over ZigBee as follows. Unlike ZigBee, Bluetooth provides communication without employing CSMA/CA and with channels switched at a frequency of about 1600 times per second, and therefore, can provide more stable communication by suppressing performance reduction in a stepwise manner while severe interference is occurring.

As described above, the receiver 36 as the trigger unit causes the controller 34 to transition from the resting state to the operational state, based on a change in the external environment of the foot switch 30. Generally, the X-ray diagnosis apparatus 10 is installed in the examination room Ri that is dedicated thereto, and the foot switch 30 is used in this examination room Ri. Therefore, a change in the external environment of the foot switch 30 is supposed to occur when the examination room Ri is being used, that is, when it is highly likely that the X-ray diagnosis apparatus 10 is to be used. Thus, the receiver 36 is configured to be able to detect such a change in the environment and restore the controller 34 from the resting state to the operational state before the procedure performer M1 uses the foot switch 30. In this embodiment, the foot switch 30 is configured to acknowledge, as a trigger for the restoration, receipt of radio signals indicating that X-ray can be radiated, specifically, the door switch signal indicating that the door Di of the examination room Ri is closed and the "examination start signal" indicating that an "examination start" command is input. As described above, direct acquisition of information from the X-ray diagnosis apparatus 10 allows highly precise prediction as to use of the X-ray diagnosis apparatus 10.

Furthermore, in this embodiment, the receiver 36 operates by converting part of input radio signals into power, and standby power for the receiver 36 is therefore not needed, so that power consumption is more effectively reduced. Note that the battery unit 35 may be configured to supply power to the receiver 36. This configuration slightly increases standby power in the resting state, but can more reliably bring the receiver 36 into operation.

Furthermore, in this embodiment, as illustrated in FIG. 4, the operation sequence of the foot switch 30 is configured to start from the resting state and automatically put the foot switch 30 into the operational state after the power to the foot switch 30 is turned on. This operation sequence makes it possible to avoid the foot switch 30 from staying in the operational state in the event that, after the power to the foot switch 30 is turned on, the stop instruction is not issued while the components of the X-ray diagnosis system 1 other than the foot switch 30 are yet to be started up. However, depending on how the X-ray diagnosis system 1 is operated, the operation sequence of the foot switch 30 may be configured to start from the operational state.

Note that, although two conditions, which are a door of an examination room being closed and a state ready for "starting an examination", are set as requirements for transition of the foot switch 30 from the resting state to the operational state in this embodiment, only one of these conditions may be set as a requirement or three or more conditions may be set as requirements.

Figure 6:
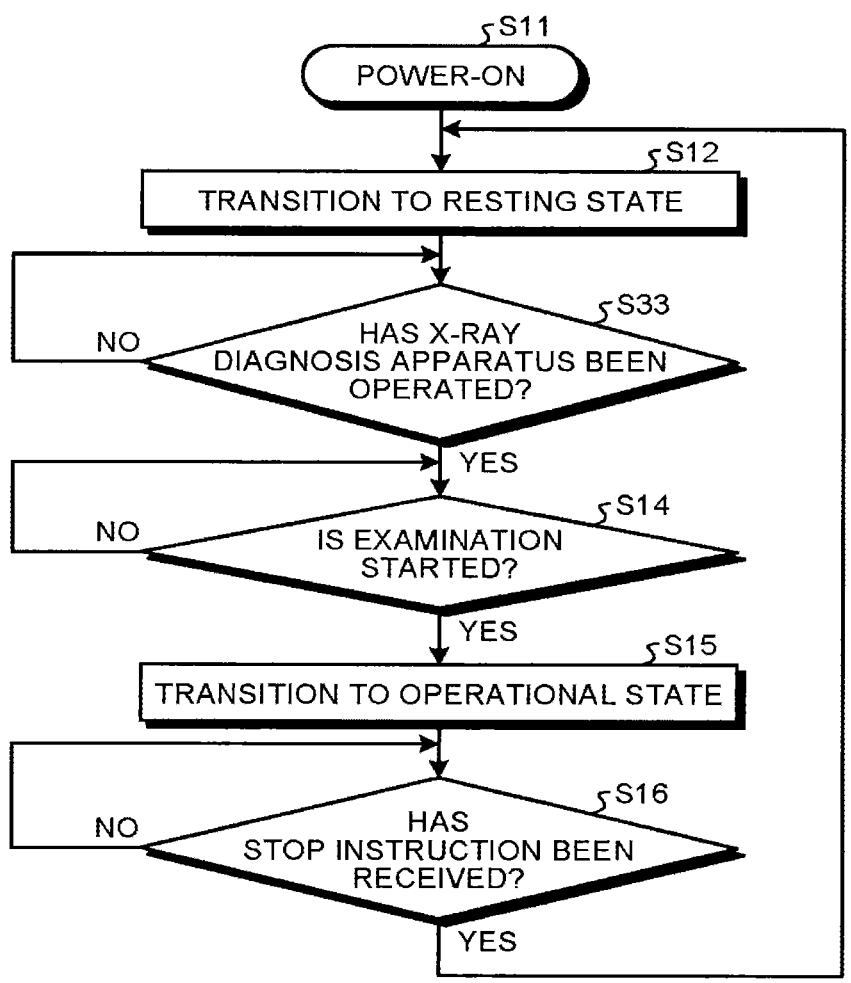
FIG. 6 is a flowchart diagram illustrating operations of a wireless foot switch according to a second embodiment.

The following describes a second embodiment. FIG. 6 is a flowchart diagram illustrating operations of a wireless foot switch according to this embodiment.

As illustrated in FIG. 6, the wireless foot switch according to this embodiment is different from the wireless foot switch (refer to FIG. 4) according to the above-described first embodiment in that, as a requirement for transition from the resting state to the operational state, having an X-ray diagnosis apparatus operated is used instead of having a door of an examination room closed. In other words, the operation sequence of a foot switch includes Step S33 instead of Step S13 (refer to FIG. 4).

Specifically, at Step S33 in FIG. 6, when the X-ray diagnosis apparatus 10 is released from the "radiation-disabled" state or when the bed driving mechanism 17 is operated, an operation notification signal indicating it is issued by the control unit 19 through the antenna 22. The receiver 36 of the foot switch then receives this operation notification signal. The process then proceeds from Step S33 to Step S14. Step S14 may be carried out before Step S13 with the order of Steps S33 and S14 reversed. Alternatively, Step 333 and Step S14 may be carried out in parallel.

Also according to this embodiment, the foot switch can automatically transition from the resting state to the operational state by detecting that the X-ray diagnosis apparatus 10 has become operable for X-ray radiation. The configurations, operations and effects in this embodiment other than the described ones are the same as those in the above-described first embodiment. For example, the sequence of operations of the foot switch 30 may be started with the operating state, depending on how the X-ray diagnosis system 1 is operated. Additionally, although this embodiment employs, as requirements for causing the foot switch 30 to transition from the resting state to the operating state, the conditions that the X-ray diagnosis apparatus has been operated and that the apparatus is ready for "staring an examination", this is not a limiting example. For example, only any one of the above conditions may be employed as the requirement, or three or more conditions may be employed as the requirements. In one example, the condition that a door of the examination room is closed may be employed as the requirement in addition to the conditions that the X-ray diagnosis apparatus has been operated and that the apparatus is ready for "staring an examination".

Figure 7:
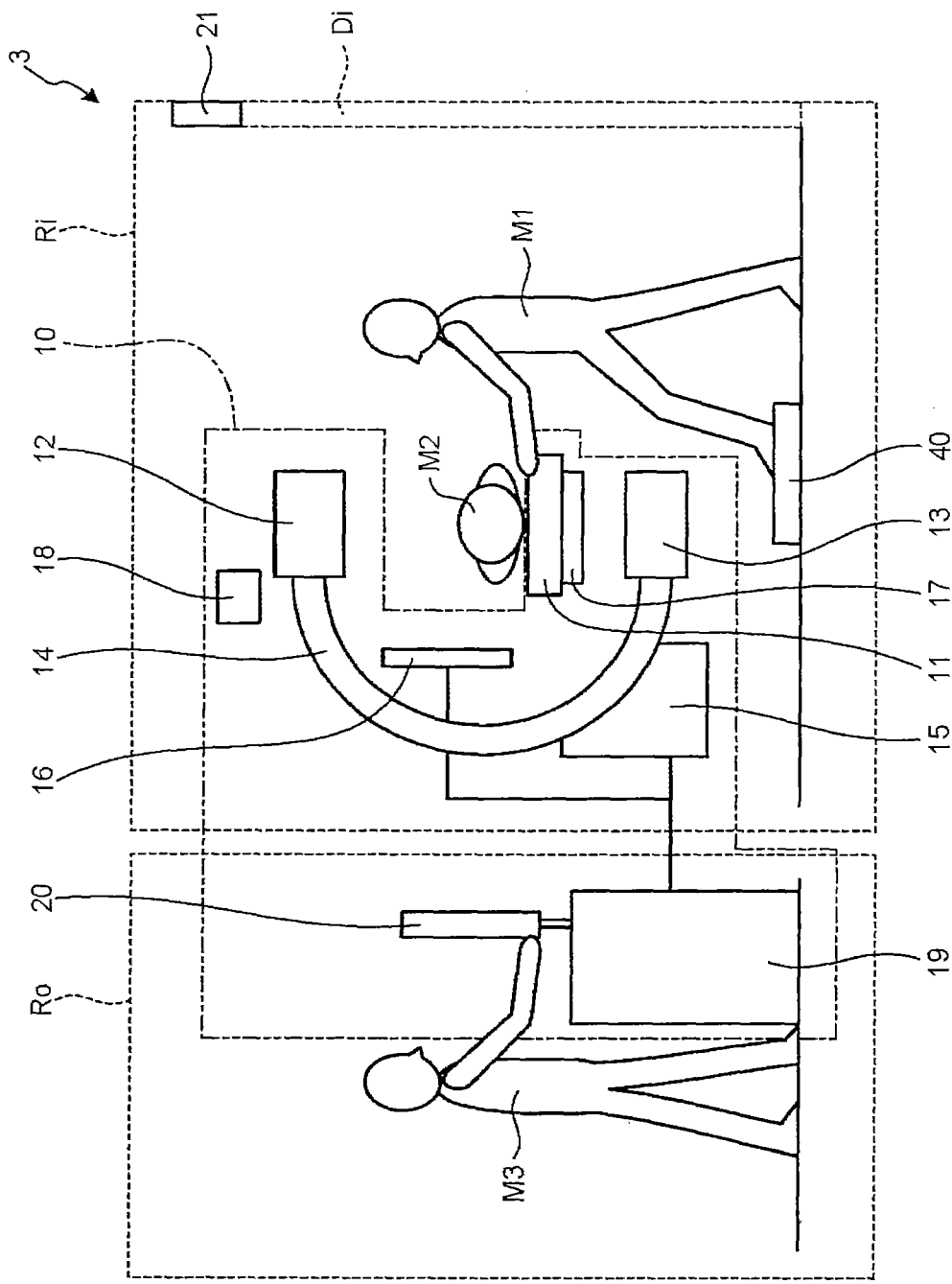
FIG. 7 is a diagram exemplifying an X-ray diagnosis system according to a third embodiment.
Figure 8:
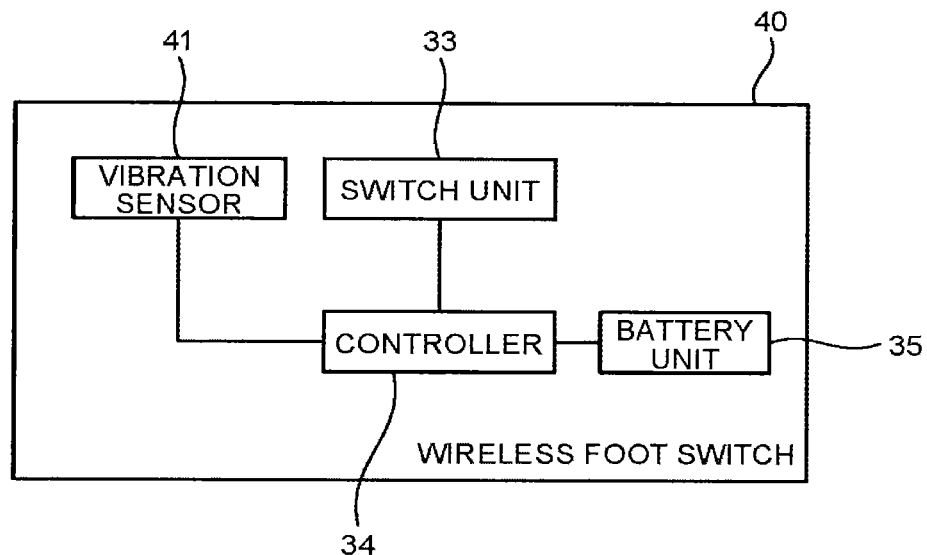
FIG. 8 is a block diagram exemplifying a wireless foot switch according to the third embodiment.

The following describes the third embodiment. In the third embodiment, a case where transition between states is based on vibration, which is an external stimulus, is described. FIG. 7 is a diagram exemplifying an X-ray diagnosis system according to this embodiment. FIG. 8 is a block diagram exemplifying a wireless foot switch according to this embodiment.

As illustrated in FIG. 7, an X-ray diagnosis system 3 according to this embodiment differs from the X-ray diagnosis system 1 (refer to FIG. 1) according to the above-described first embodiment in that the antenna 22 is not included. Because of this configuration, the control unit 19 does not issue radio signals indicating that the X-ray diagnosis apparatus has become operable to radiate X-rays, that is, the door switch signal, the examination start signal, and the operation notification signal. In addition, a foot switch 40 is included instead of the foot switch 30 (refer to FIG. 1).

As illustrated in FIG. 8, the wireless foot switch 40 according to this embodiment includes a vibration sensor 41 as a trigger unit (also referred to as a detector). The vibration sensor 41 is, for example, an acceleration sensor and outputs a trigger signal to the controller 34 upon detecting vibration. For example, the battery unit 35 supplies power to the vibration sensor 41 through the controller 34.

Figure 9:
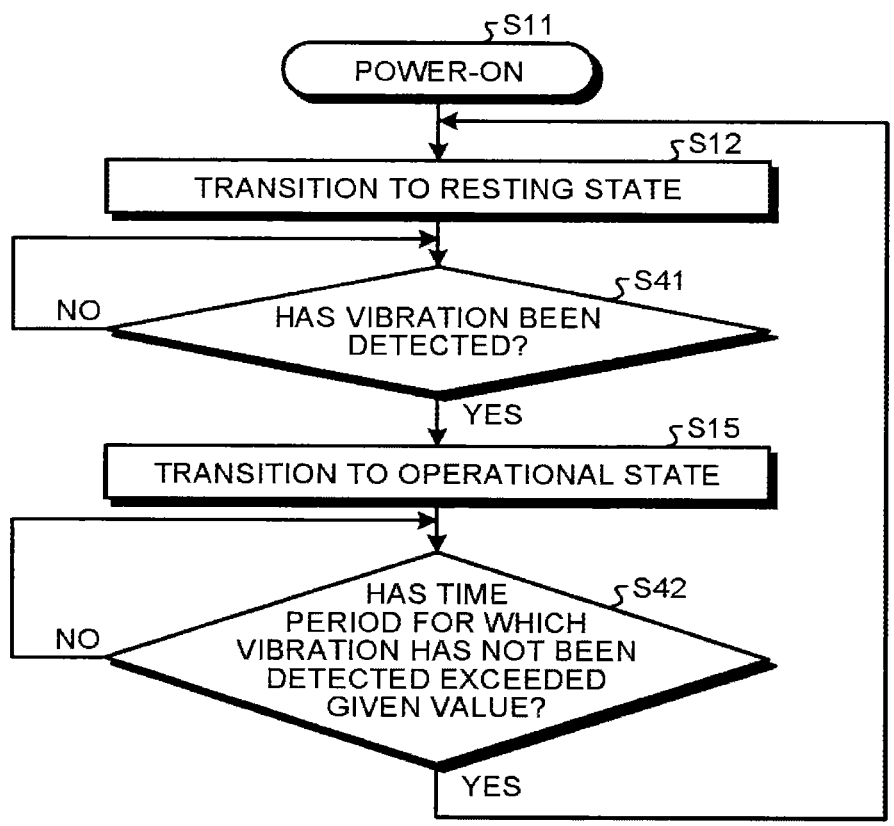
FIG. 9 is a flowchart diagram illustrating operations of the wireless foot switch according to the third embodiment.

Next, operations of the wireless foot switch according to this embodiment are described. FIG. 9 is a flowchart diagram illustrating operations of the wireless foot switch according to this embodiment.

First, when the power to the wireless foot switch 40 is turned on at the start as illustrated in Step S11 in FIG. 9, the controller 34 enters into the resting state as illustrated in Step S12. Subsequently, at Step S41, upon detection of vibration, the vibration sensor 41 generates the trigger signal and outputs the signal to the controller 34. When the signal is thus input, the controller 34 enters into the operational state as illustrated in Step S15. Note that input of an "examination start signal" may be set as a condition for transition to the operational state, in addition to detection of vibration. Such condition setting is described in a sixth embodiment described below.

It is assumed that kinds of vibration that the vibration sensor 41 detects are the following <1> to <4>: <1> vibration caused when the procedure performer M1 and a technologist moves inside the examination room; <2> vibration caused when the X-ray diagnosis apparatus 10 operates; <3> vibration caused when an impact is applied to the wireless foot switch; and <4> vibration caused when the wireless foot switch is being carried around.

When the vibration sensor 41 detects vibration because of the above <1> to <4>, it is highly likely that there is a person being inside the examination room Ri and in motion. It is assumed that this is when work in the examination room, that is, a procedure with the X-ray diagnosis apparatus 10 or preparation thereof is started, and it is likely that the X-ray diagnosis apparatus 10 is about to be used. Thus, with the foot switch 40 having transitioned from the resting state to the operational state upon detection of vibration, the foot switch 40 can be immediately operated when use of the X-ray diagnosis apparatus 10 is attempted.

Thereafter, as illustrated in Step S42, if a time period for which the vibration sensor 41 has not detected vibration exceeds a given value, the process returns to Step S12, where the foot switch 40 transitions to the resting state. When the vibration sensor 41 has not detected vibration for a given period of time, it is highly likely that no work is conducted in the examination room, and it is therefore appropriate to cause the foot switch 40 to transition to the resting state.

Next, effects of this embodiment are described. As described above, in this embodiment, the vibration sensor 41 as a trigger unit detects vibration as a change in the external environment of the foot switch 40, thereby detecting the presence of a person in the examination room Ri. This detection enables prediction as to use of the X-ray diagnosis apparatus 10 and enables the foot switch 40 to transition to the operational state prior to the use. In configuring this embodiment, it is not necessary to modify the components of a conventional X-ray diagnosis system other than the foot switch 40. Therefore, the same effects as those of the above-described first embodiment can be achieved with ease and at low cost. The configurations, operations and effects in this embodiment other than the described ones are the same as those in the above-described first embodiment.

For example, the sequence of operations of the foot switch 40 may be started with the operating state, depending on how the X-ray diagnosis system 3 is operated. Additionally, although this embodiment employs detection of vibration as a requirement for causing the foot switch 40 to transition from the resting state to the operating state, this is not a limiting example. For example, a radio signal indicating that X-ray radiation is allowed (for example, the door switch signal, the examination start signal, and the operation notification signal) may be employed as the requirement in addition to detection of vibration. This example is described in detail in the sixth embodiment.

Figure 10:
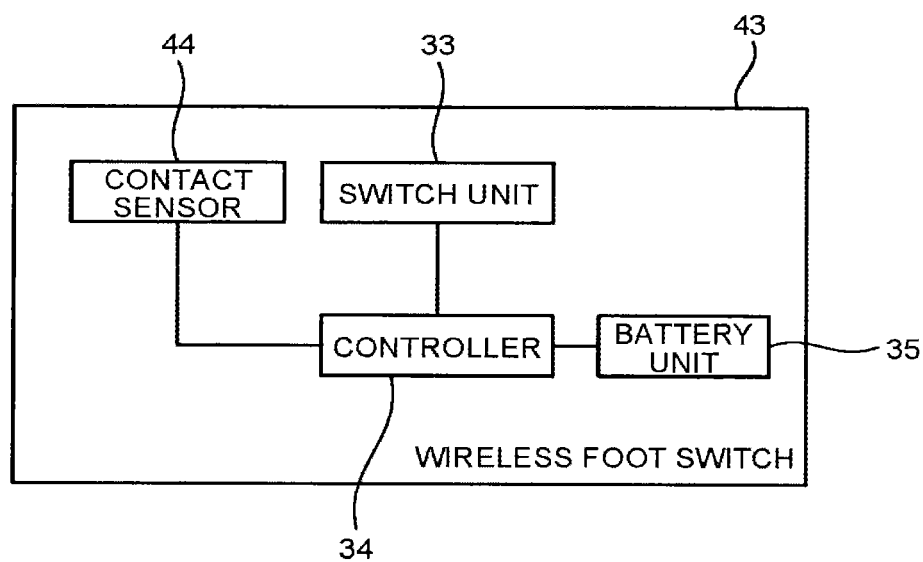
FIG. 10 is a block diagram exemplifying a wireless foot switch according to a fourth embodiment.
Figure 11A:
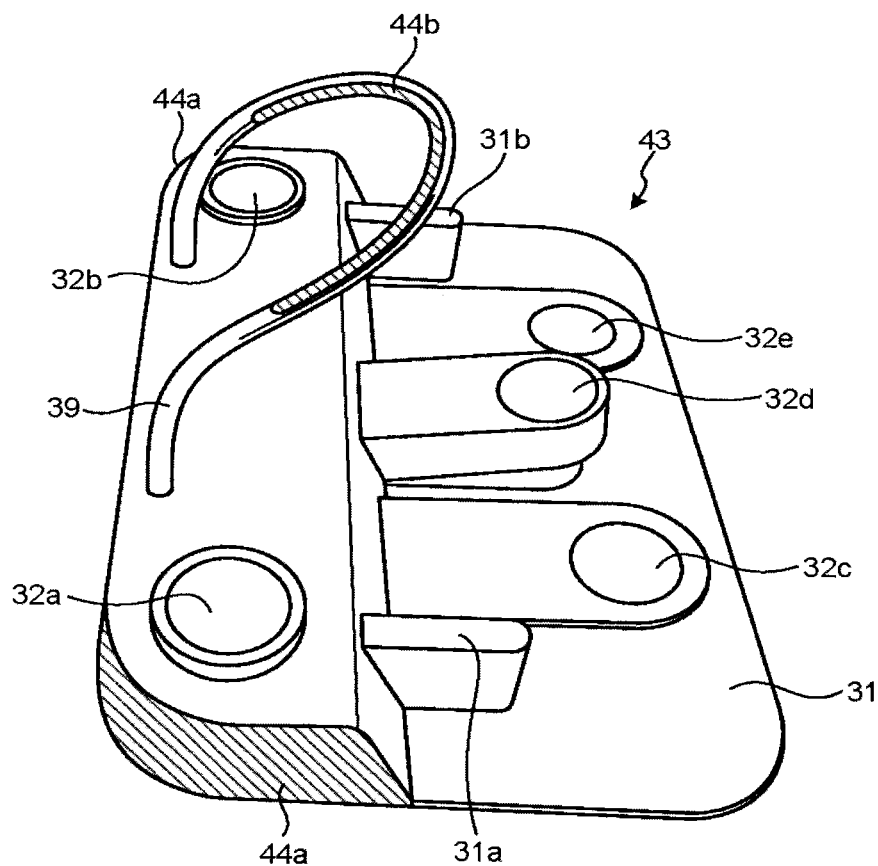
FIGS. 11A and 11B are perspective views exemplifying a wireless foot switch according to the fourth embodiment.
Figure 11B:
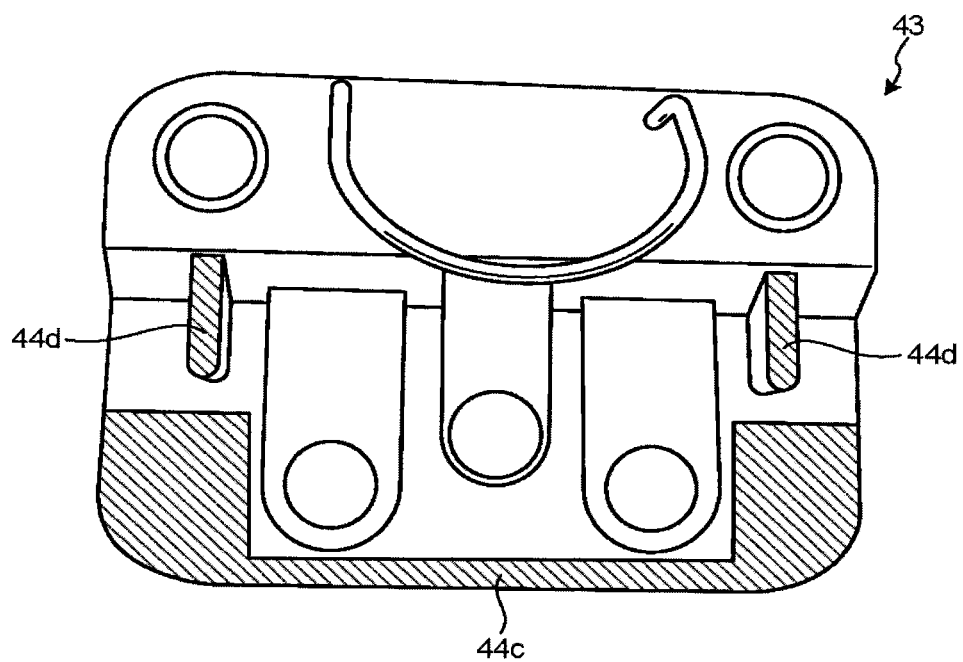

Next, a fourth embodiment is described. In the fourth embodiment, a case where transition between the states is based on contact, which serves as an external stimulus, is described. FIG. 10 is a block diagram exemplifying the wireless foot switch according to this embodiment. FIGS. 11A and 112 are perspective views exemplifying the wireless foot switch according to this embodiment. As illustrated in FIG. 10 and FIGS. 11A and 11B, the wireless foot switch 43 according to this embodiment includes a contact sensor 44 that detects contact. The contact sensor 44 is arranged on the outer surface of the housing 31 and on the outer surface of the protector 39. Specifically, the contact sensor 44 includes: a pair of corner sections 44*a* arranged in corner regions of opposite sides of the hinder part of the housing 31; a loop section 44*b* arranged on the outside surface of the loop portion in the upper part of the protector 39; a fore-part section 44*c* arranged on the top surface of the fore part of housing 31; a pair of guide top-surface sections 44*d* arranged on the respective top surfaces of the guide portions 31*a* and 31*b* of the housing 31. However, the arrangement of the contact sensor 44 is not limited to this example.

Figure 12:
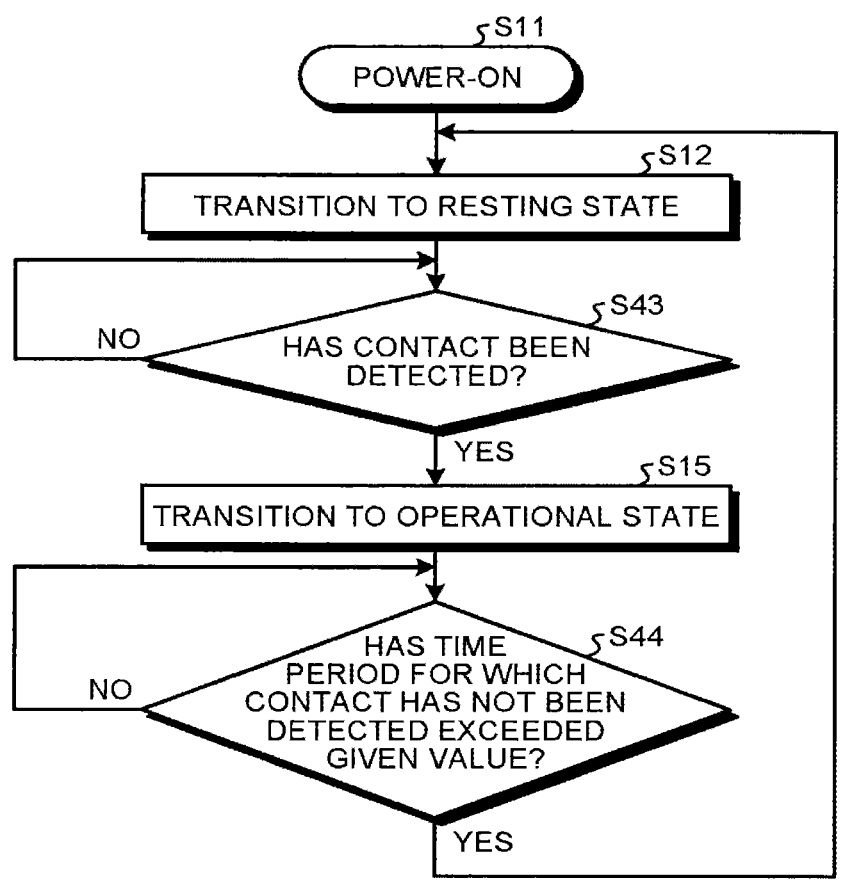
FIG. 12 is a flowchart diagram illustrating operations of the wireless foot switch according to the fourth embodiment.

Next, operations of the wireless foot switch according to this embodiment are described. FIG. 12 is a flowchart diagram illustrating operations of the wireless foot switch according to this embodiment.

First, when the power to the wireless foot switch 43 is turned on as illustrated in Step S11 in FIG. 12, the controller 34 enters into the resting state as illustrated in Step S12. Subsequently, at Step S43, upon detection of contact, the contact sensor 44 generates a trigger signal and outputs the signal to the controller 34. In response to this signal, the controller 34 enters into the operational state as illustrated in Step S15.

It is assumed that the contact sensor 44 detects contact in the following cases <1> and <2>: <1> contact made by a person such as a procedure performer when the person moves the wireless foot switch to a operational position; and <2> contact made to some part other than the pedals during preparation for photographing.

Regarding the above case <1>, it is considered that, when moving the foot switch 43, a person such as a procedure performer grips the loop portion 44*b* with a hand or catches the loop portion 44*b* with a foot to move the foot switch 43, and that the body of the person such as a procedure performer is highly likely to make contact with the corner portions 44*a* and the loop portion 44*b*. Regarding the above case <2>, it is considered that a procedure performer is highly likely to place a foot on the fore-part section 44*c* or the guide top-surface sections 44*d* of contact sensor 44 when preparing for photographing.

Therefore, when the contact sensor 44 detects contact, it is highly likely that the foot switch 43 is being carried around or has a foot of a procedure performer placed thereon, and it is highly likely that the X-ray diagnosis apparatus 10 is about to be used. Thus, previously returning the foot switch 43 to the operational state when the contact sensor 44 detects contact enables the procedure performer to immediately operate the foot switch 43 when starting to use the X-ray diagnosis apparatus 10.

Thereafter, as illustrated in Step S44, when a time period for which the contact sensor 44 has not detected contact exceeds a given value, the process returns to Step S12, where the foot switch 43 transitions to the resting state. When the contact sensor 44 has not detected contact for a given period of time, the procedure performer is highly likely to be apart from the foot switch 43, and it is therefore appropriate to bring the foot switch 43 into the resting state.

Next, effects of this embodiment are described. In this embodiment, as in the case of the third embodiment, it is not necessary to modify the components of a conventional X-ray diagnosis system other than the foot switch 43. Therefore, the same effects as those of the above-described first embodiment can be achieved with ease and at low cost. The configurations, operations and effects in this embodiment other than the described ones are the same as those in the above-described third embodiment. For example, the sequence of operations of the foot switch 43 may be started with the operating state, depending on how the X-ray diagnosis system 3 is operated. Additionally, although this embodiment employs detection of contact as a requirement for causing the foot switch 43 to transition from the resting state to the operating state, this is not a limiting example. For example, detection of vibration or a radio signal indicating that X-ray radiation is allowed (for example, the door switch signal, the examination start signal, and the operation notification signal) may be employed as the requirement in addition to detection of contact.

Figure 13:
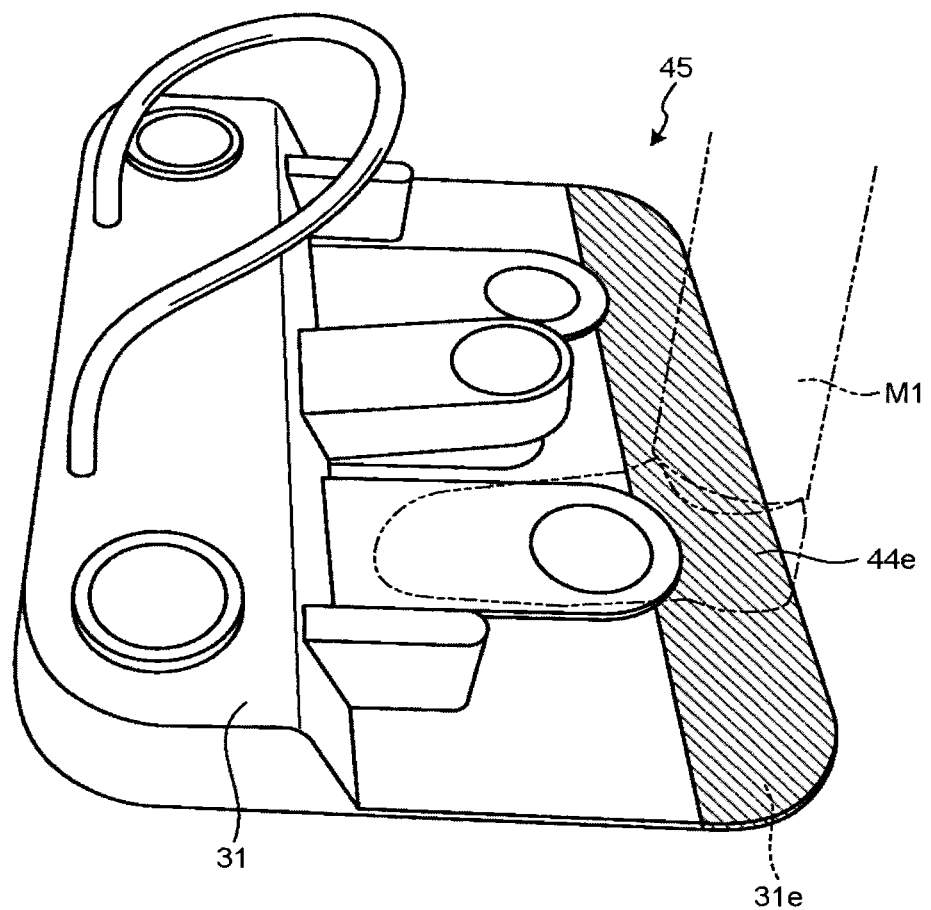
FIG. 13 is a perspective view exemplifying a foot switch according to a modification example of the fourth embodiment.

Next, a modification example of the fourth embodiment is described. FIG. 13 is a perspective view exemplifying a foot switch according to this modification example. As illustrated in FIG. 13, the wireless foot switch 45 according to this modification example differs from the foot switch 43 according to the above-described fourth embodiment in that the housing 31 is extended forward to form an extended portion 31*e*, on which the procedure performer M1 can put a heel. Additionally, an extended section 44*e* of the contact sensor 44 is arranged on the top surface of the extended portion 31*e* of the housing 31.

This configuration allows the extended section 44*e* of the contact sensor 44 to detect that a procedure performer puts a heel on the extended portion 31*e* of the housing 31 so as to use the foot switch 45, and the controller 34 is caused to transition from the resting state to the operational state. This configuration also makes it possible to have the foot switch 45 automatically returned to the operational state before the foot switch 45 is actually operated. The configurations, operations and effects in this modification example other than the described ones are the same as those in the above-described fourth embodiment.

Figure 14:
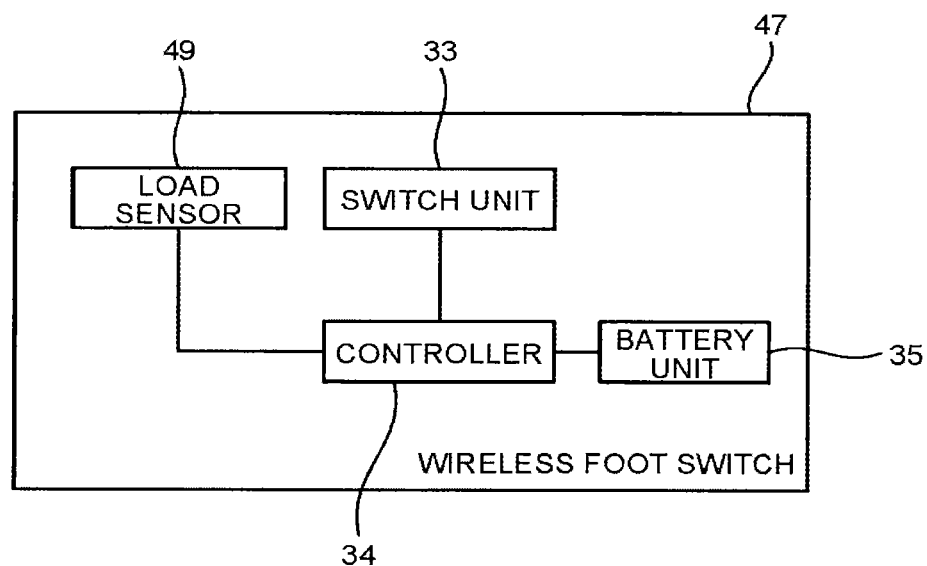
FIG. 14 is a block diagram exemplifying a wireless foot switch according to a fifth embodiment.
Figure 15:
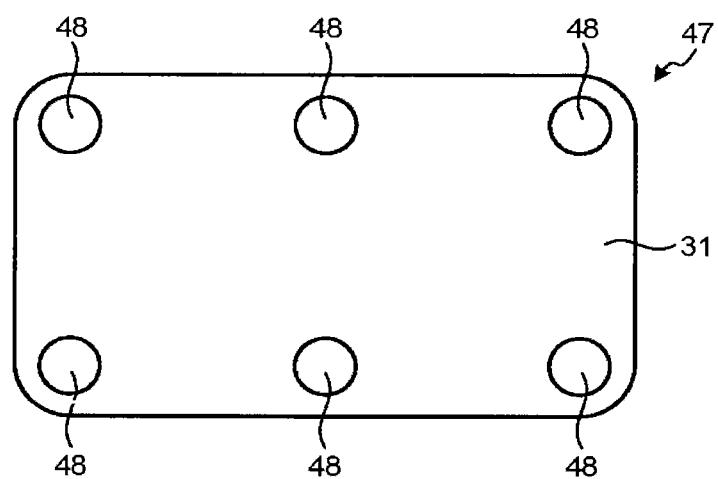
FIG. 15 is a bottom view exemplifying a wireless foot switch according to the fifth embodiment.

Next, a fifth embodiment is described. In the fifth embodiment, a case where transition between the states is based on pressure (a load), which serves as an external stimulus, is described. FIG. 14 is a block diagram exemplifying a wireless foot switch according to this embodiment. FIG. 15 is a bottom view exemplifying the wireless foot switch according to this embodiment.

As illustrated in FIG. 14 and FIG. 15, a wireless foot switch 47 according to this embodiment includes a leg or a plurality of legs 48 at one or a plurality of positions on the bottom surface of the housing 31, for example, at six positions. The leg 48 is supported with a spring. A load sensor 49 as a trigger unit is attached to the top end of the leg 48. This configuration causes the leg 48 to enter into the inside of the housing 31 when a downward load is applied to the wireless foot switch 47 while the wireless foot switch 47 is placed on the floor. As a result, the load sensor 49 detects the load. At the same time, the load sensor 49 generates a trigger signal and output the signal to the controller 34 to cause the controller 34 to transition from the resting state to the operational state.

Figure 16:
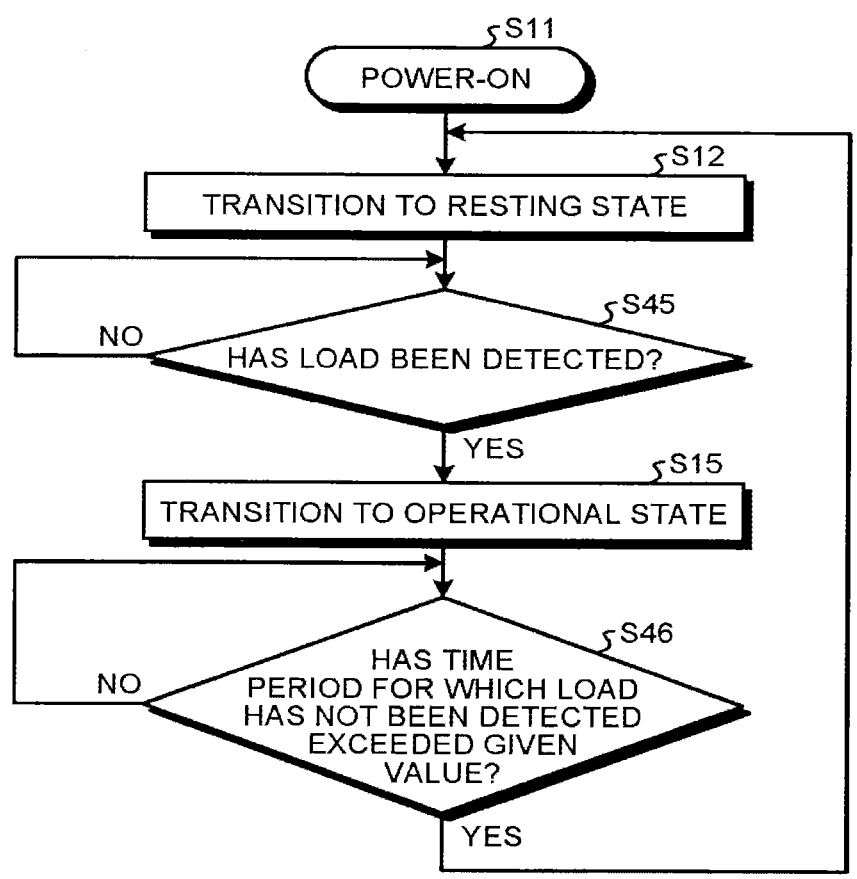
FIG. 16 is a flowchart diagram illustrating operations of the wireless foot switch according to the fifth embodiment.
Figure 17:
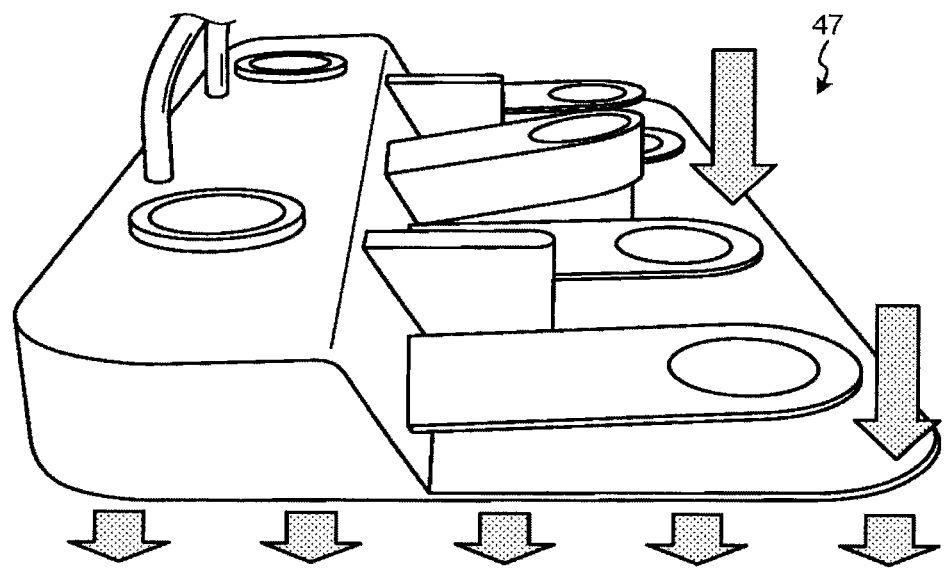
FIG. 17 is a perspective view illustrating operations of the wireless foot switch according to the fifth embodiment.

Next, operations of the wireless foot switch according to this embodiment are described. FIG. 16 is a flowchart diagram illustrating operations of the wireless foot switch according to this embodiment. FIG. 17 is a perspective view illustrating operations of the wireless foot switch according to this embodiment. Note that this embodiment is an example where the foot switch includes seven pedals as illustrated in FIG. 17.

First, when the power to the wireless foot switch 47 is turned on as illustrated in Step S11 in FIG. 16, the controller 34 enters into the resting state as illustrated in Step S12. Subsequently, as illustrated in Step S45 of FIG. 16 and in FIG. 17, a downward load is applied to the housing 31 when a procedure performer places a foot on the housing 31 of the wireless foot switch 47. The housing 31 and the leg 48 are pressed in directions in which the housing 31 and the leg 48 become closer to each other, so that the load sensor 49 detects the load. Subsequently, the load sensor 49 generates a trigger signal and outputs the signal to the controller 34, so that the controller 34 is caused to enter into the operational state as illustrated in Step S15. Thereafter, as illustrated in Step S46 in FIG. 16, when a time period for which the load sensor 49 has not detected a load exceeds a given value, the process returns to Step S12, where the controller 34 is caused to transition to the resting state.

Next, effects of this embodiment are described. This embodiment also makes it possible to return the foot switch 47 automatically to the operational state before it is used, without modification of components in the X-ray diagnosis system other than the foot switch 47. The configurations, operations and effects in this embodiment other than the described ones are the same as those in the above-described third embodiment. For example, the operation sequence of the foot switch 47 may be started with the operating state, depending on how the X-ray diagnosis system 3 is operated. Additionally, although this embodiment employs detection of a load as a requirement for causing the foot switch 47 to transition from the resting state to the operating state, this is not a limiting example. For example, detection of vibration, detection of contact, or a radio signal indicating that X-ray radiation is allowed (for example, the door switch signal, the examination start signal, and the operation notification signal) may be employed as the requirement in addition to detection of a load.

Figure 18:
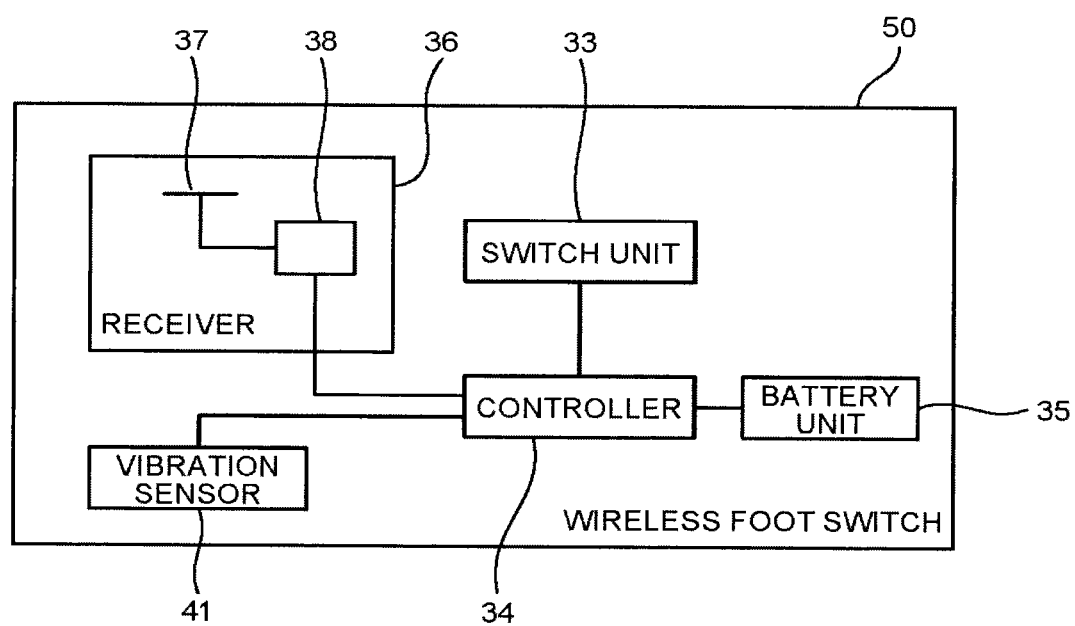
FIG. 18 is a block diagram exemplifying a wireless foot switch according to a sixth embodiment.

Next, the sixth embodiment is described. FIG. 18 is a block diagram exemplifying a wireless foot switch according to this embodiment. This embodiment is an example obtained by combining the above-described first embodiment and third embodiment and further adding several functions to a resultant of the combination.

The X-ray diagnosis system according to this embodiment is the same as the X-ray diagnosis system 1 illustrated in FIG. 1. In other words, the X-ray diagnosis system includes the antenna 22. As illustrated in FIG. 18, the wireless foot switch 50 according to this embodiment includes, as a trigger unit, the receiver 36 and the vibration sensor 41. Thus, the foot switch 50 transitions from the resting state to the operational state when the receiver 36 receives an "examination start signal" issued by the X-ray diagnosis apparatus 10 and the vibration sensor 41 detects vibration.

On the other hand, the foot switch 50 transitions from the operational state to the resting state on condition that: the receiver 36 receives a stop instruction from the X-ray diagnosis apparatus 10; a time period for which the vibration sensor 41 has not detected vibration exceeds a given value; or the remaining power amount of the battery unit 35 is below a given value. Additionally, the foot switch 50 displays its state, for example, whether it is in the operational state or in the resting state, and the remaining power amount of the battery unit 35 on the examination room panel 16 of the X-ray diagnosis apparatus 10.

Next, operations of the X-ray diagnosis system according to this embodiment are described. FIG. 19 is a flowchart diagram exemplifying operations of the wireless foot switch according to this embodiment.

First, as illustrated in Step S51 in FIG. 19, the power to the wireless foot switch 50 is turned on. This step causes the foot switch 50 to start up. Thereafter, as illustrated in Step S52, the foot switch 50 transitions to the resting state. The X-ray diagnosis apparatus 10 is notified via radio communication that the foot switch 50 has transitioned to the resting state, and this notification is displayed on the examination room panel 16.

Next, as illustrated in Step S53, it is determined whether the receiver 36 has received an "examination start signal" from the X-ray diagnosis apparatus 10, and the process proceeds to Step S54 if the receiver 36 has. Next, as illustrated in Step S54, it is determined whether the vibration sensor 41 has detected vibration, and the process proceeds to Step S55 if the vibration sensor 41 has. Step S54 may be carried out before Step S53 with the order of Steps S53 and S54 reversed. Alternatively, Step S53 and Step S54 may be carried out in parallel.

At Step S55, the foot switch 50 transitions from the resting state to the operational state. This transition enables the X-ray diagnosis apparatus 10 to be operated with a switch unit 33. Additionally, the X-ray diagnosis apparatus 10 is notified via radio communication that the foot switch 50 has transitioned to the operational state, and this notification is displayed on the examination room panel 16.

Thereafter, as illustrated in Steps S56 to S58, the process returns to Step S52 on condition that: the receiver 36 receives a "stop instruction" from the X-ray diagnosis apparatus 10; a time period for which the vibration sensor 41 has not detected vibration exceeds a given value; or the remaining power amount of the battery unit 35 is below a given value. At Step S52, the foot switch 50 transitions from the operational state to the resting state. Thereafter, a loop from Step S52 to Step S58 is repeated until the power to the foot switch 50 is turned off.

Next, effects of this embodiment are described. The foot switch 50 according to this embodiment transitions from the resting state to the operational state on condition that a command for "examination start" has been input to the X-ray diagnosis apparatus 10 and that the vibration sensor 41 detects vibration. Thus, even when there is a person entering and leaving the examination room for such a purpose as cleaning the inside of the room while examinations are not being conducted, the foot switch 50 can be prevented from undesirably transitioning to the operational state, and therefore, power consumption can be effectively reduced.

Furthermore, the foot switch 52 according to this embodiment transitions to the resting state when a "stop instruction"

is received or when a time period for which vibration has not been detected exceeds a given value. This configuration can reliably bring the foot switch 50 into the resting state when the foot switch 50 is not being used, and therefore can reduce power consumption more effectively.

Furthermore, in this embodiment, the foot switch 50 is configured to transition to the resting state when the remaining power amount of the battery unit 35 is below a given value. This configuration makes it possible to more effectively avoid the battery of the foot switch 50 from running out while the X-ray diagnosis apparatus 10 is in use.

Furthermore, in this embodiment, the state of the foot switch 50, for example, whether it is the resting state or the operational state, and the remaining power amount of the battery unit 35 are displayed on the examination room panel 16. This configuration enables the procedure performer M1 to know a condition of the foot switch 50 during a manipulation without largely changing the direction of eyes to check the condition. As a result, efficiency and safety in practicing of a procedure are improved.

Note that, although an example in this embodiment is such that the receiver 36 and the vibration sensor 41 are included as a trigger unit, this is not a limiting example. For example, the contact sensor 44 and the load sensor 49 may be included in addition to and used together with the receiver 36 and the vibration sensor 41 or selectively. Although an example in this embodiment is such that the receiver 36 receives the examination start signal, the receiver 36 may be configured to receive at least one of the door switch signal indicating that the door of the examination room is closed and the operation notification signal indicating that the X-ray diagnosis apparatus 10 has been operated, and these signals are used together or selectively. Furthermore, in addition to the trigger unit, pedaling any one the pedals 32 may be adopted as a way to cancel the resting state. Using such a plurality of ways in combination enables the foot switch to effectively switch between states in accordance with the manner in which the foot switch is operated. Additionally, for example, the sequence of operations of the foot switch 50 may be started with the operating state, depending on how the X-ray diagnosis system 1 is operated.

Although the first and the second embodiments exemplify the examination start signal, the door switch signal, and the operation notification signal as signals that are transmitted from the X-ray diagnosis apparatus 10 and that cause the foot switch to transition from the resting state to the operational state in, this is not a limiting example. These signals may be, for example, radio signals that indicate that X-ray diagnosis apparatus 10 has become operable to radiate X-rays. On the other hand, as a signal for causing the foot switch to transition from the operational state to the resting state, a signal indicating that the right to make selection on the examination room panel 16 and the right to make selection on the operation room panel 20 are both cancelled.

The above-described first embodiment is described with exemplary reference to the case where a signal indicating that the door of the examination room is closed is used as an external signal. However, this is not a limiting example, and a signal based on weight acting on the couchtop on which a subject lies, a signal indicating that there is a person in the examination room, or a signal based on light inside the examination room may be used as an external signal.

For example, a load sensor (pressure sensor) provided to the couchtop detects a load (pressure) acting on the couchtop, and a transmitter provided to the couchtop transmits a detection signal to the receiver 36. A trigger signal that the receiver 36 has generated based on the detection signal causes the controller 34 to transition to the operational state. Here, the load sensor (pressure sensor) provided to the couchtop may be set so as to transmit the detection signal when the load (pressure) acting on the couchtop exceeds a predetermined threshold. This setting enables lying down of a subject on the couchtop to trigger the foot switch to transition to the operational state.

Additionally, in a configuration where the state transition is caused by a signal indicating that there is a person in the examination room, a signal indicating that there is a person near a position at which a manipulation is conducted on a subject. In one example of this configuration, sensor such as a human-presence sensor, an infrared sensor, or a pressure sensor is provided near the couchtop or near a position at which the foot switch is placed, the state transition is caused based on detection signals detected by the sensor. In another example, sensor such as a human-presence sensor, an infrared sensor, or a pressure sensor is provided at any position in the examination room (for example, near the door of the examination room or near the examination room panel), and the state transition is caused based on detection signals detected by the sensor. In this case, the receiver 36 receives detection signals transmitted from the sensor and generates a trigger signal. The trigger signal generated by the receiver 36 based on the detection signals causes the controller 34 to transition to the operational state.

Alternatively, the signal indicating that there is a person in the examination room may be, for example, acquired from an image of the examination room captured by a camera. In one example of this acquisition, an image processing apparatus installed in the operation room or the examination room performs image processing on an image captured by a camera installed in the examination room and determines whether the image depicts a person. Here, if the image depicts a person, the image processing apparatus transmits a detection signal to the receiver 36. The receiver 36 generates a trigger signal based on the received detection signal and transmits the signal to the controller 34, so that the controller 34 is caused to transition to the operational state, by the trigger signal transmitted from the receiver 36.

Note that, when an image captured by a camera is used, the detection signal may be transmitted based on, for example, determination as to whether there is a person lying on the couchtop or whether the image depicts at least a predetermined number or persons.

Furthermore, when the state transition is caused by a signal based on light in the examination room, for example, a signal indicating that brightness in the examination room is changed. In one example, a photosensor is provided in the examination room, the state transition is caused based on a detection signal detected by the photosensor. In this case, the receiver 36 receives the detection signal transmitted from the photosensor and generates a trigger signal. The controller 34 is caused to transition to the operational state, by the trigger signal that the receiver 36 has generated based on the detection signal. When a manipulation is conducted in the examination room, brightness in the examination room changes, for example, with a light turned on when a subject lies, with a light turned off for the manipulation, or with an astral lamp turned on. Thus, the photosensor transmits the detection signal to the receiver 36 at the time when the brightness has transitioned from a high state to a low state or at the time when the brightness has transitioned from a low state to a high state.

As described above, the wireless foot switch according to the present application can cause state transition based on various external signals. Note that, from the above-described external signals (such as the signal indicating that the door is closed, a signal based on a weight acting on the couchtop on which a subject lies, a signal indicating that there is a person in the examination room, and the signal based on light in the examination room), only one signal or a plurality of signals in combination may be used.

Additionally, the external-signal based state transition described above and the external-stimulus based state transition described above may be implemented in an appropriate combination. For example, when the vibration sensor detects vibration after the signal indicating that the door is closed is received, the controller 34 may be controlled so as to transition to the operational state.

Furthermore, each of the above-described third to fifth embodiments and in the modification example thereof exemplifies a case using a vibration sensor, a contact sensor or a load sensor as a trigger unit. Each of these sensors is broadly defined as a human-presence sensor that detects the presence of a person in the examination room. However, a human-presence sensor is not limited to these examples, and an infrared sensor employing a pyroelectric element may be employed as a human-presence sensor.

Furthermore, although each of the above-described embodiments exemplifies the case where the X-ray diagnosis apparatus is an X-ray imaging apparatus, this is not a limiting example. The X-ray diagnosis apparatus may be, for example, a computed tomography (CT) examination apparatus or a mammography apparatus.

The above-described embodiments can provide a wireless foot switch for an X-ray diagnosis apparatus and an X-ray diagnosis system that operate for extended operating times.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A wireless foot switch comprising:
a battery unit that supplies power;
a switch unit that provides input to an X-ray diagnosis apparatus;
a controller that transmits information to the X-ray diagnosis apparatus by radio, the information having been input by the switch unit; and
a state switcher that, based on an external signal from the outside of the X-ray diagnosis apparatus, causes the controller to transition from a resting state to an operational state.

2. The wireless foot switch according to claim 1, wherein the state switcher includes a receiver that receives an external signal indicating that the X-ray diagnosis apparatus has become operable for radiating X-rays.

3. The wireless foot switch according to claim 2, wherein the external signal is at least one signal out of a signal indicating that a door of an examination room inside of which the X-ray diagnosis apparatus radiates X-rays is closed, a signal based on weight acting on a couchtop on which a subject lies, a signal indicating that there is a person in the examination room, and a signal based on light in the examination room.

4. The wireless foot switch according to claim 3, wherein the signal indicating that there is a person in the examination room is a signal indicating that there is a person near a position where a manipulation is conducted on the subject.

5. The wireless foot switch according to claim 3, wherein the signal based on light in the examination room is a signal indicating that brightness in the examination room has changed.

6. The wireless foot switch according to claim 1, wherein, based on an examination start signal in addition to the external signal, the state switcher causes the controller to transition from the resting state to the operating state.

7. The wireless foot switch according to claim 2, wherein
the receiver receives, as signals indicating that the X-ray diagnosis apparatus has become operable for radiating X-rays, in addition to the external signal, a signal indicating that the X-ray diagnosis apparatus has been operated and a signal indicating that the X-ray diagnosis apparatus is released from a state where radiation of X-rays is disabled, and
the state switcher causes the controller to transition from a resting state to an operational state, based on at least one signal out of the external signal, the signal indicating that the X-ray diagnosis apparatus has been operated, and the signal indicating that the X-ray diagnosis apparatus is released from a state where X-ray radiation is disabled.

8. The wireless foot switch according to claim 2, wherein the receiver operates by converting part of the external signal into power.

9. An X-ray diagnosis system comprising:
the wireless foot switch according to claim 1; and
the X-ray diagnosis apparatus.

10. A wireless foot switch comprising:
a battery unit that supplies power;
a switch unit that provides input to an X-ray diagnosis apparatus;
a controller that transmits information by radio to the X-ray diagnosis apparatus, the information having been input by the switch unit;
a detector that detects an external stimulus; and
a state switcher that, based on the external stimulus, causes the controller to transition from a resting state to an operational state.

11. The wireless foot switch according to claim 10, wherein the detector detects at least any of vibration, pressure, and contact, as the external stimulus.

12. The wireless foot switch according to claim 10, wherein, based on an examination start signal in addition to the external stimulus, the state switcher causes the controller to transition from the resting state to the operating state.

13. The wireless foot switch according to claim 10, wherein, based on at least any of the external stimulus, the signal indicating that the X-ray diagnosis apparatus has been operated, and the signal indicating that the X-ray diagnosis apparatus has been released from a state where X-ray radiation is disabled, the state switcher causes the controller to transition from a resting state to an operational state.

14. An X-ray diagnosis system comprising:
the wireless foot switch according to claim 10; and
the X-ray diagnosis apparatus.

* * * * *